United States Patent [19]

Hamaoka et al.

[11] Patent Number: 4,681,856

[45] Date of Patent: Jul. 21, 1987

[54] MURAMYLDIPEPTIDE ACTIVE ESTER DERIVATIVES

[75] Inventors: Toshiyuki Hamaoka, Nara; Hiromi Fujiwara, Hyogo; Tsuneo Kusama, Tokyo, all of Japan

[73] Assignee: Toshiyuki Hamaoka Daiichi Seiyaku Co., Ltd., Japan

[21] Appl. No.: 641,905

[22] Filed: Aug. 20, 1984

[30] Foreign Application Priority Data

Aug. 18, 1983 [JP] Japan .................................. 58-149617

[51] Int. Cl.$^4$ ............................................ C08B 37/00
[52] U.S. Cl. ..................................................... 536/53
[58] Field of Search .................... 260/112.5 R; 536/53

[56] References Cited

FOREIGN PATENT DOCUMENTS 1570625 2/1980 United Kingdom .

OTHER PUBLICATIONS

Hamaoka et al., *Chemical Abstracts*, 103, 689 (1985), abst. No. 71711 p.
Kusumoto et al., *Bulletin of the Chemical Society of Japan*, 51(7), 2122–2126 (1978).

*Primary Examiner*—Delbert R. Phillips
*Attorney, Agent, or Firm*—Sughrue, Mion, Zinn Macpeak & Seas

[57] ABSTRACT

Muramyldipeptide active ester derivatives represented by the formula:

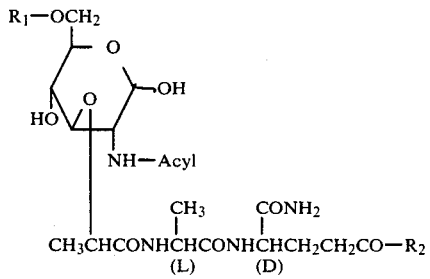

wherein $R_1$ represents a straight or branched chain fatty acid residue having 2 to 30 carbon atoms; $R_2$ represents an active ester residue; and "Acyl" represents an acyl group having 2 to 6 carbon atoms. These compounds are applicable as haptens for the immunotherapy and exhibit antitumor activity.

8 Claims, No Drawings

MURAMYLDIPEPTIDE ACTIVE ESTER DERIVATIVES

FIELD OF THE INVENTION

This invention relates to novel muramyldipeptide active ester derivatives having excellent antitumor activity. More particularly, this invention relates to muramyldipeptide active ester derivatives represented by the formula (I):

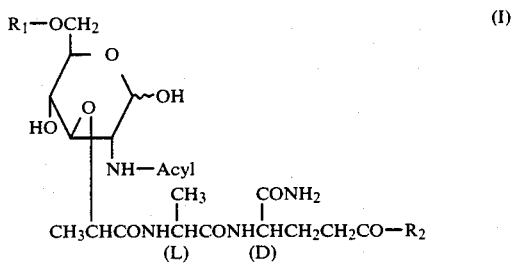

wherein $R_1$ represents a straight or branched chain fatty acid residue having 2 to 30 carbon atoms; $R_2$ represents an active ester residue; and "Acyl" represents an acyl group having 2 to 6 carbon atoms.

BACKGROUND OF THE INVENTION

With the recent development of study on enhancement of immune response aiming at antitumor effect, further detailed studies on immunological antitumor activities have been conducted.

Enhancement of immune response includes enhancements of humoral immunity, cell-mediated immunity, macrophage function, etc. With respect to cell-mediated immunity, an attempt to enhance effector T cells (hereinafter referred to as "$T_E$ cells") have been investigated.

$T_E$ cells receive a great deal of attention since they, when induced in a living organism, react specifically with tumor cells produced in the living organism to destroy the tumor cells.

The present inventors considered the mechanism of $T_E$ cells generation in a living organism as summarized in what follows.

In case normal cells are transformed into tumor cells, "tumor associated antigens" appeared in the tumor cells. On the other hand, in the case when tumor bearing hosts are immunized with hapten-modified autologous cells, hapten-reactive helper T cells are induced. The induced hapten-reactive helper T cells enhance generation of $T_E$ cells specific to the tumor cells. The $T_E$ cells recognize the tumor associated antigens and destroy the tumor cells.

The term "hapten" herein used means an incomplete antigen which per se lacks immunogenicity but, upon being conjugated to autologous serum proteins or autologous cell surfaces, potentially induces T cell activity in vivo.

The present inventors found 2,4,6-trinitrophenyl group (TNP) to be capable of playing a role as a hapten exhibiting immune response specific to tumor cells and proved the above-described reaction mechanism (J. Exp. Med. 149 185-199 (1979) and J. Immunol. 124 863-869 (1980)). However, application of this immunotherapy to tumors in human is not satisfactory in view of toxicity of TNP and the like.

SUMMARY OF THE INVENTION

The present inventors made various attempts to find a substance suitable as a hapten that is easily conjugated to surfaces of tumor cells by mixing therewith to potentiate tumor specific immunity, is of low toxicity and is clinically applicable. As a result, it has now been found that active ester derivatives of muramyl-dipeptides represented by the above-described formula (I) satisfy the above requirements and the present inventors completed the invention.

In addition, it is hitherto known that tubercle bacillus (*Bacillus tuberculosis*) has potential immunogenicity to not only animals but humans from the fact that subcutaneous injection of tuberclin protein or tubercle bacillus-related substances to the person who has been inoculated with BCG vaccine induces tuberclin hypersensitivity.

Therefore, if the compound according to the present invention shares antigenic determinants to BCG, the compound of this invention per se would presumably induce tumor specific immunity, without induction of hapten-reactive helper T cells, to people whose tuberclin-negative state has been converted to a tuberclin-positive state spontaneously or by BCG vaccination. This possibility is of great clinical advantage.

Examinations based on the above-described viewpoint confirmed that the compound according to the present invention shares antigenic determinants to BCG and ensured the effectiveness of the compound of this invention.

DETAILED DESCRIPTION OF THE INVENTION

In the above-described formula (I), the active ester residue represented by $R_2$, which characterizes the compounds of the present invention, includes a phenyl ester residue, e.g., a p-nitrophenol group, a 2,4-dinitrophenol group, a 2,4,5-trichlorophenol group, a pentachlorophenol group, a pentafluorophenol group, a thiophenol group, etc.; an N-hydroxyamine ester residue, e.g., an N-hydroxysuccinimido group, an N-hydroxybenzotriazole group, an N-hydroxy-5-norbornene-2,3-dicarboximido group, an N-hydroxyphthalimido group, an N-hydroxymorpholine group, an N-hydroxypiperidine group, etc.; and a bifunctional ester residue, e.g., a 2-mercaptopyridine group, a 2-hydroxypyridine group, a 3-hydroxypyridine group, an 8-hydroxyquinoline group, a 2-hydroxyphenol group, etc., preferably an N-hydroxy-5-norbornene-2,3-dicarboximido group, a 2-hydroxypyridine group or a 3-hydroxypyridine group.

The fatty acid residue represented by $R_1$ having a total carbon number of 2 to 30 specifically includes acetyl group, butyryl group, hexanoyl group and octanoyl group.

The compound of the formula (I) of this invention can be prepared by reacting a compound represented by the formula (II):

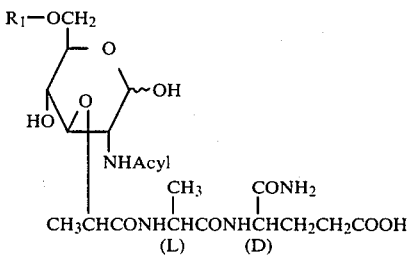

$$\text{(II)}$$

CH₃CHCONHCHCONHCHCH₂CH₂COOH
(L)         (D)

with structure showing CH₃ and CONH₂ substituents wherein R₁ is as defined above,
with a compound represented by the formula (III):

$$H-R_2 \qquad \text{(III)}$$

wherein R₂ is as defined above, according to a condensation process generally employed for peptide synthesis, preferably a carbodiimide process.

The condensation by a carbodiimide method is carried out by reacting the compound (II) with the compound (III) in the presence of dicyclohexylcarbodiimide in a solvent, such as acetonitrile, tetrahydrofuran, chloroform, N,N-dimethylformamide, dimethyl sulfoxide, pyridine, etc., and a mixture thereof, at a temperature of from about 0° C. to about 80° C., preferably from 20° C. to 40° C., for a period of from about 1 hour to about 2 days. In this reaction, dicyclohexylcarbodiimide is used in an amount of about 1 to about 2 mols, preferably 1.0 to 1.2 mols, per mol of the compound (II), and the compound (III) is used in an amount of about 1 to about 2 mols, preferably 1.0 to 1.2 mols, per mol of the compound (II). The compound (I) can be isolated from the reaction mixture by conventional method commonly employed in peptide synthesis, such as extraction, solvent fractionation, reprecipitation, recrystallization, gel chromatography, etc.

The present invention will now be illustrated in greater detail with reference to Examples and Test Examples which are given for illustrative purposes only and the present invention is not limited thereto.

EXAMPLE 1

0.10 g of 6-O-acetyl-N-acetylmuramyl-L-alanyl-D-isoglutamine and 24 mg of N-hydroxysuccinimide were dissolved in 2 ml of N,N-dimethylformamide, and 1 ml of an N,N-dimethylformamide solution containing 46 mg of dicyclohexylcarbodiimide was added to the solution under ice-cooling while stirring. After 2 hours, the reaction mixture was allowed to warm to room temperature, and the stirring was continued overnight. The precipitated dicyclohexylurea was removed by filtration, and the filtrate was concentrated under reduced pressure. To the resulting syrup was added diethyl ether, and the precipitated powder was taken out by filtration. Recrystallization of the powder from a mixture of acetonitrile and diethyl ether gave 87 mg of 6-O-acetyl-N-acetylmuramyl-L-alanyl-D-isoglutamine 1-succinimidyl ester as a white powder.

Rf=0.24 (thin layer chromatography; silica gel; chloroform:methanol:water=8:3:1 lower layer).

IR (IBr): 3380, 2980–2930, 1815, 1780, 1735, 1650, 1540, 1245–1210 cm⁻¹.

$[\alpha]_D^{25} + 25.2°$ (c 0.9, N,N-dimethylformamide).

Elementary Analysis for $C_{25}H_{37}O_{14}N_5 \cdot H_2O$: Calculated (%): C 46.21, H 6.06, N 10.78. Found (%): C 46.42, H 6.04, N 10.58.

EXAMPLE 2

1.80 g of 6-O-butyryl-N-acetylmuramyl-L-alanyl-D-isoglutamine and 0.64 g of N-hydroxy-5-norbornene-2,3-dicarboximide were dissolved in 70 ml of tetrahydrofuran. To the resulting solution was then added 20 ml of a tetrahydrofuran solution containing 0.79 g of dicyclohexylcarbodiimide under ice-cooling while stirring. After 2 hours, the reaction temperature was allowed to warm to room temperature, and the stirring was continued overnight, followed by filtration to remove the precipitated dicyclohexylurea. The filtrate was concentrated under reduced pressure, and diethyl ether was added to the resulting syrup, followed by filtration to obtain a powder. The powder was recrystallized from a mixture of acetonitrile and diethyl ether to yield 2.11 g of 6-O-butyryl-N-acetyl-L-alanyl-D-isoglutamine 5-norbornene-2,3-dicarboxyimidyl ester as a white powder.

Rf=0.37 (thin layer chromatography; silica gel; chloroform:methanol:water=8:3:1 lower layer).

IR (KBr): 3350, 2960–2860, 1815, 1780, 1730, 1665, 1525, 1200 cm⁻¹.

$[\alpha]_D^{25} + 30.9°$ (c 1.5, tetrahydrofuran).

Elementary Analysis for $C_{32}H_{45}O_{14}N_5 \cdot \frac{1}{2}H_2O$: Calculated (%): C 52.44, H 6.34, N 9.56. Found (%): C 52.49, H 6.30, N 9.37.

EXAMPLE 3

The same procedures as described in Example 2 were repeated except for using 0.3 g of 6-O-hexanoyl-N-acetylmuramyl-L-alanyl-D-isoglutamine in place of 6-O-butyryl-N-acetylmuramyl-L-alanyl-D-isoglutamine to obtain 0.26 g of 6-O-hexanoyl-N-acetylmuramyl-L-alanyl-D-isoglutamine 5-norbornene-2,3-dicarboximidyl ester as a white powder.

Rf=0.41 (thin layer chromatography; silica gel; chloroform:methanol:water=8:3:1 lower layer).

IR (KBr): 3350, 2950–2860, 1815, 1780, 1725, 1650, 1530, 1210 cm⁻¹.

$[\alpha]_D^{25} + 29.0°$ (c 0.6, tetrahydrofuran).

Elementary Analysis for $C_{34}H_{49}N_5O_{14} \cdot \frac{1}{2}H_2O$: Calculated (%): C 53.67, H 6.62, N 9.21. Found (%): C 53.52, H 6.53, N 9.18.

EXAMPLE 4

0.13 g of 6-O-octanoyl-N-acetylmuramyl-L-alanyl-D-isoglutamine and 22 mg of 3-hydroxypyridine were dissolved in 3 ml of tetrahydrofuran, and 2 ml of a tetrahydrofuran solution containing 48 mg of dicyclohexylcarbodiimide was added thereto under ice-cooling while stirring. After 2 hours, the reaction mixture was allowed to warm to room temperature, and the stirring was continued overnight. The precipitated dicyclohexylurea was removed by filtration, and the filtrate was concentrated under reduced pressure. To the resulting syrup was added diethyl ether. The thus-precipitated powder was taken out by filtration and dissolved in a small amount of acetonitrile. 85 ml of a diethyl ether solution containing 40 mg of p-toluenesulfonate monohydrate was added to the resulting solution, followed by filtration to obtain the precipitated powder. The powder was recrystallized from a mixture of acetonitrile and diethyl ether to obtain 0.12 g of 6-O-octanoyl- N-acetylmuramyl-L-alanyl-D-isoglutamine 3-pyridyl ester p-toluenesulfonate as a white powder.

Melting Point: 100°–102° C.

$[\alpha]_D^{25} +35.6°$ (c 0.5, tetrahydrofuran).

Elementary Analysis for $C_{34}H_{49}N_5O_{12}\cdot C_7H_8O_3S\cdot H_2O\cdot\frac{1}{2}CH_3CN$: Calculated (%): C 52.99, H 6.74, N 8.50. Found (%): C 52.74, H 6.71, N 8.73.

EXAMPLE 5

0.45 g of 6-O-(2-tetradecylhexadecanoyl)-N-acetylmuramyl-L-alanyl-D-isoglutamine, 87 mg of N-hydroxy-5-norbornene-2,3-dicarboximide were dissolved in 2 ml of tetrahydrofuran, and 1 ml of a tetrahydrofuran solution containing 0.10 g of dicyclohexylcarbodiimide was added to the solution under ice-cooling while stirring. After 2 hours, the reaction mixture was allowed to warm to room temperature, followed by stirring for 2 days. The precipitated dicyclohexylurea was removed by filtration, and the filtrate was concentrated under reduced pressure. The resulting syrup was subjected to gel-filtration chromatography using Sephadex LH-20 and eluted with dioxane. The active fractions containing the desired product were collected and lyophylized. The resulting powder was ice-cooled and washed with acetonitrile to obtain 0.33 g of 6-O-(2-tetradecylhexadecanoyl)-N-acetylmuramyl-L-alanyl-D-isoglutamine 5-norbornene-2,3-dicarboxyimidyl ester as a white powder.

Melting Point: 86°–88° C.

$[\alpha]_D^{25} +38.7°$ (c 1.0, tetrahydrofuran).

Elementary Analysis for

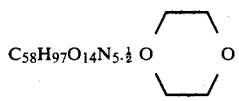

Calculated (%): C 63.62, H 9.01, N 6.18. Found (%): C 63.44, H 8.81, N 6.12.

EXAMPLE 6

100 mg of 6-O-butyryl-N-acetylmuramyl-L-alanyl-D-isoglutamine and 27.2 mg of p-nitrophenol were dissolved in 3 ml of acetonitrile, and 1 ml of an acetonitrile solution containing 40.3 mg of dicyclohexylcarbodiimide was added thereto under ice-cooling and stirring. After 30 minutes, the reaction temperature was allowed to warm to room temperature. The stirring was continued overnight, followed by filtration to remove the precipitated dicyclohexylurea. The filtrate was concentrated under reduced pressure, and to the resulting syrup was added diethyl ether. The precipitated powder was taken out by filtration. Recrystallization of the powder from tetrahydrofuran-diethyl ether gave 70.5 mg of 6-O-butyryl-N-acetylmuramyl-L-alanyl-D-isoglutamine p-nitrophenyl ester as a white powder.

Rf=0.35 (thin layer chromatography; silica gel; chloroform:methanol:water=8:3:1 lower layer).

IR (KBr): 3350, 2960–2930, 1760, 1720, 1650, 1520, 1345, 1200, 860, 745 cm$^{-1}$.

$[\alpha]_D^{25} +40.5°$ (c=0.5, tetrahydrofuran).

Elementary Analysis for $C_{29}H_{41}N_5O_{14}\cdot\frac{1}{2}H_2O$: Calculated (%): C 50.28, H 6.11, N 10.11. Found (%): C 50.33, H 6.25, N 10.01.

The biological activities of the compounds (I) according to the present invention were confirmed by the following Test Examples 1 to 6. The compounds of the invention used in these test examples are as follows:

Compound No. 1: 6-O-Butyryl-N-acetylmuramyl-L-alanyl-D-isoglutamine 5-norbornene-2,3-dicarboxyimidyl ester Compound No. 2: 6-O-Hexanoyl-N-acetylmuramyl-L-alanyl-D-isoglutamine 5-norbornene-2,3-dicarboxyimidyl ester Compound No. 3: 6-O-Octanoyl-N-acetylmuramyl-L-alanyl-D-isoglutamine 3-pyridyl ester p-toluenesulfonate.

TEST EXAMPLE 1

Shared Antigenic Determinant between Compound of Invention and BCG

I. Test Animal:

Group A: C57BL/6 mice received two subcutaneous injections (1 mg of BCG) at three weeks interval.

Group B: C57BL/6 mice received no injection of BCG.

II. Preparation of MDP-Related Hapten-Modified Autologous Cells:

One to five millimols of Compound No. 1 and syngeneic mouse spleen cells ($10^8$) from which erythrocytes had been removed were incubated at 37° C. for 20 minutes with shaking. The cells were then washed with a 5% fetal bovine serum-containing culture medium, RPMI 1640, to prepare 6-O-butyryl-N-acetylmuramyl-L-alanyl-D-isoglutamine-modified syngeneic spleen cells (hereinafter referred to as "L4-MDP-modified syngeneic spleen cells"), i.e., MDP-related hapten-modified autologous cells.

III. Test for Confirmation of Shared Antigenic Determinant (in delayed-type hypersensitivity response):

The MDP-related hapten-modified autologous cells ($1\times10^6$) were subcutaneously injected to the hind footpad of each test animal, and footpad swellings were determined after 24 hours and 48 hours. Control groups were injected with Hanks+ balanced salt solution. An increase of swelling in each test group indicates the existence of shared antigenic determinant between the test compound and BCG. The results are shown in Table 1.

TABLE 1

| | Delayed-Type Hypersensitivity Response Induced by L4-MDP-Modified Syngeneic Spleen Cells | |
|---|---|---|
| Test | | Footpad Increment ($10^{-2}$ mm)* |
| Group | Treatment | At 24 Hrs. / At 48 Hrs. |
| A | Control | 4.7 ± 2.3 / 0.0 |
| | L4-MDP-modified syngeneic spleen cells | 24.7 ± 1.2 / 16.7 ± 1.8 |
| B | Control | 4.3 ± 2.0 / 0.0 |
| | L4-MDP-modified syngeneic spleen cells | 11.0 ± 2.3 / 8.3 ± 2.1 |

Note:
*Means ± standard error.

TEST EXAMPLE 2

Potent Immunogenic Activity of Compound of Invention as Hapten

I. Preparation of Test Cells:

Responding cells that reflect reactivity of test animals were prepared as follows:

L4-MDP-modified syngeneic spleen cells ($5\times10^7$) as prepared according to Test Example 1 were subcutaneously injected three times to a BALB/C mouse at weekly intervals, and the spleen cells were prepared from the immunized mouse. The resulting spleen cells are designated as Responding Cells (1). On the other hand, spleen cells were prepared from a non-immunized BALB/C mouse and are designated as Responding Cells (2).

Further, as MDP-related hapten-modified autologous cells, L4-MDP-modified syngeneic spleen cells (designated as "Stimulating Cells (A)") and syngeneic spleen cells which are not modified with L4-MDP (designated as "Stimulating Cells (B)") were prepared.

II. Test for Confirmation of Potent Immunogenic Activity as Hapten:

Responding Cells (1) or (2) ($4 \times 10^5$/well) were cultured with Stimulating Cells (A) or (B) ($4 \times 10^5$/well) in a Falcon microculture plate (3072) at 37° C. for 5 days. On the fourth day, 1 $\mu$Ci/well of tritiated thymidine was added to the culture. On the fifth day, the cells were harvested, and the amount of tritiated thymidine incorporated in the cells was measured. An increase of this amount indicates that the proliferative response of T cells was induced, i.e., the tested compound has suitability as a hapten. The results obtained are shown in Table 2.

TABLE 2
T Cell Proliferative Response Induced by
L4-MDP-Modified Syngeneic Spleen Cells Immunization

| Responding Cells | Stimulating Cells | Tritiated Thymidine Incorporation (cpm) |
|---|---|---|
| (1) | (A) | 19,405 |
|  | (B) | 4,320 |
| (2) | (A) | 8,241 |
|  | (B) | 1,102 |

TEST EXAMPLE 3

Induction of Helper T Cells by Compound of Invention

I. Preparation of MDP-Related Hapten-Modified Autologous Cells:

In accordance with the procedures described in Test Example 1, the following syngeneic spleen cells modified with Compound No. 1, 2 or 3, i.e., MDP-related hapten-modified autologous cells, were prepared:

With Compound No. 1: L4-MDP-modified syngeneic spleen cells

With Compound No. 2: L6-MDP-modified syngeneic spleen cells

With Compound No. 3: L8-MDP-modified syngeneic spleen cells.

II. Preparation of Test Model:

(A) Preparation of Helper T Cell Source:

Each of the aforesaid MDP-related hapten-modified autologous cells ($5 \times 10^7$) were subcutaneously injected twice to a C57BL/6 mouse for immunization. The spleen cells from the immunized mouse were irradiated with 850R X-rays to obtain a helper T cell source ($3 \times 10^6$/well). On the other hand, spleen cells from a non-immunized C57BL/6 mouse were irradiated with X-rays in the same manner as above to prepare a control cell source ($3 \times 10^6$/well).

(B) Preparation of Responding Cells ($T_E$ Cell Source):

Spleen cells separated from a C57BL/6 mouse ($3.5 \times 10^6$/well) were used.

(C) Preparation of Stimulating Cells:

Syngeneic spleen cells ($1 \times 10^6$/well) modified with N-iodoacetyl-N'-(5-sulfonic-1-naphthyl)ethylenediamine, which is regarded as a model of a tumor-associated antigen (i.e., a hapten other than the MDP-related compounds; hereinafter referred to as AED), syngeneic spleen cells ($1 \times 10^6$/well) modified with 1 mM of Compound Nos. 1 to 3, and a mixture of these two kinds of spleen cells were prepared.

III. Test for Confirmation of Helper T Cell Induction:

The aforesaid helper T cell source, the responding cells and the stimulating cells were mixed and incubated at 37° C. for 5 days. After the incubation, RBL5 syngeneic tumor cells which had been conjugated to AED and further labelled with $^{51}$Cr were mixed with the cultured cells as target cells. Cell lysis of the RBL5 syngeneic tumor cells was determined according to the $^{51}$Cr release assay [J. Immunol. Vol. 124, No. 2, 863–869 (1980)] and expressed in terms of cytotoxicity. The higher the cytotoxicity, the higher the induction of $T_E$ cells, i.e., the higher the induction of helper T cells. The results are shown in Table 3 below. It was proved by these results that immunization with the syngeneic spleen cells modified with the compounds of the present invention can induce helper T cells reactive with the compounds of the invention.

TABLE 3
Helper T Cells Induced by Immunization with
MDP-Related Hapten-Modified Syngeneic Spleen Cells

| Helper T Cell Source | Cytotoxicity (%) Effector Cell:Target Cell Ratio | | | |
|---|---|---|---|---|
|  | 5:1 | 10:1 | 20:1 | 40:1 |
| Spleen cells immunized with L4-MDP-modified syngeneic spleen cells | 7.4 | 6.7 | 14.8 | 22.3 |
| Control | 6.8 | 2.4 | 9.7 | 9.8 |
| Spleen cells immunized with L6-MDP-modified syngeneic spleen cells | — | 4.6 | 9.5 | 11.1 |
| Control | — | 2.2 | 2.1 | 4.3 |
| Spleen cells immunized with L8-MDP-modified syngeneic spleen cells | — | 8.7 | 13.9 | 20.0 |
| Control | — | 4.1 | 9.5 | 12.8 |

The above results are obtained when using a mixture of AED-modified syngeneic spleen cells and L4-MDP-modified syngeneic spleen cells as stimulating cells. In the case of using each of them individually under the same test conditions, no significant production of cytotoxicity was observed.

TEST EXAMPLE 4

Study on whether or no Helper T Cells Reactive to Compounds of the Invention Are Present in Spleen Cells of BCG-Immunized Mice I. Preparation of Test Model:

(A) Preparation of Helper T Cell Source:

A C3H/HeN mouse was twice immunized by subcutaneously injecting 1 mg of BCG at three weeks interval. The spleen cells from the immunized mouse were irradiated with 850R X-rays to obtain a helper T cell source ($3.0 \times 10^6$/well). Spleen cells of a non-immunized C3H/HeN mouse were irradiated with X-rays in the same manner to prepare a control ($3.0 \times 10^6$/well).

(B) Preparation of Responding Cells (T$_E$ Cell Source):

Spleen cells (1.5×10$^6$/well) taken from a C3H/HeN mouse were used.

(C) Preparation of Stimulating Cells

Syngeneic spleen cells (1×10$^6$/well) modified with 1 mM of trinitrobenzene sulfonate, which is a model of a tumor associated antigen (i.e., a hapten other than the MDP-related compounds); syngeneic spleen cells (2×10$^6$/well) modified with 1 mM of L4-MDP; and a mixture of both were prepared.

II. Test for Confirmation of Helper T Cell Induction:

The aforesaid helper T cell source, responding cells and stimulating cells were mixed and incubated at 37° C. for 5 days. After the incubation, the incubated cells were mixed with X-5563 syngeneic tumor cells, to which TNP had been conjugated and which had further been labelled with $^{51}$Cr, as target cells. Cell lysis of the X-5563 syngeneic tumor cells was determined by a $^{51}$Cr release assay and expressed in terms of cytotoxicity. In this test, the higher the cytotoxicity, the higher the induction of T$_E$ cells. The above fact means that helper T cells which can be activated by the compounds of this invention exist in the spleen cells of BCG-immunized mice. The test results shown in Table 4 below prove the existence of L4-MDP-reactive helper T cells in the spleen cells of the BCG-immunized mouse. This fact was similarly proved in the test in which TNP-LSTRA syngeneic tumor cells were used as target cells.

TABLE 4

| Helper T Cell Activity Specific to L4-MDP in Spleen Cells from BCG-Immunized Mice | | | |
|---|---|---|---|
| Helper T Cell Source | Cytotoxicity (%) T$_E$ Cell: Target Cell Ratio | | |
|  | 5:1 | 10:1 | 20:1 |
| Spleen cells of BCG-immunized mouse | 7.5 | 12.0 | 24.5 |
| Control | 0 | 2.0 | 4.8 |

The above results of Table 4 are obtained when using a mixture of the TNP-modified syngeneic spleen cells and the L4-MDP-modified syngeneic spleen cells as stimulating cells. In the case when tests were conducted under the same conditions but using each of them individually, no significant production of the cytotoxicity was observed.

TEST EXAMPLE 5

Effect of Compound of Invention on Enhancement of Antitumor Immunity

I. Test Animal:
C3H/HeN mice

II. Preparation of Tumor Specific T$_E$ Cells in vivo:

For the purpose of inducing helper T cells reactive to the MDP-related hapten in mouse spleen cells, the L4-MDP-modified syngeneic spleen cells (5×10$^7$) were subcutaneously injected four times to the mouse for immunization. The immunized mouse further received 3 intraperitoneal injections of L4-MDP-modified syngeneic X5563 tumor cells (1×10$^7$) treated with mitomycin. The immunization with L4-MDP-modified syngeneic tumor cells aims at enhancing generation of T$_E$ cells reactive to a tumor associated antigen in the mouse spleen cells. From the treated mouse, spleen cells (1×10$^7$) were used as a treated group. As controls, spleen cells from a mouse which had been treated only with 3 intraperitoneal injections of L4-MDP-modified syngeneic X5563 tumor cells treated with mitomycin (Control Group 1) and spleen cells from a mouse which had received no treatment at all (Control Group 2) were prepared.

III. Test for Enhancement of Antitumor Immunity:

Viable X5563 cells were mixed with T$_E$ cells prepared above and inoculated subcutaneously into untreated mice. The tumor diameter was measured with the passage of time to determine the tumor growth. The same procedures were carried out on the control groups. The results as shown in Table 5 below demonstrate a remarkable inhibitory effect on tumor growth in the treated group, i.e., an activity of the compound of this invention to potentiate antitumor immunity.

Such an antitumor activity observed in the above test is specific to X5563 tumor cells but is not observed on other tumor cells, e.g., syngeneic hepatoma MH134 cells.

It was proved by this test example that the compound according to the present invention, when treated by proper immunization procedures, induces helper T cells, which, in turn, induce tumor specific T$_E$ cells thereby enhancing antitumor immunity.

TABLE 5

| Test Group | Inhibitory Effect on Tumor Growth | | | |
|---|---|---|---|---|
|  | Tumor Diameter (mm) | | | |
|  | 10th Day | 11th Day | 13th Day | 18th Day |
| Treated Group | 1.5 | 1.8 | 2.1 | 4.4 |
| Control Group 1 | 8.8 | 10.0 | 12.7 | 18.7 |
| Control Group 2 | 6.3 | 6.8 | 9.4 | 17.0 |

While the invention has been described in detail and with reference to specific embodiments thereof, it will be apparent to one skilled in the art that various changes and modifications can be made therein without departing from the spirit and scope thereof.

What is claimed is:

1. A muramyldipeptide derivative represented by the formula:

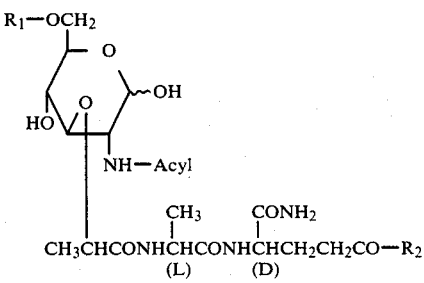

$$CH_3CHCONHCHCONHCHCH_2CH_2CO-R_2$$
$$\phantom{CH_3CHCONH}\overset{CH_3}{|}\phantom{CONHCH}\overset{CONH_2}{|}$$
(L) (D)

wherein R$_1$ represents a straight or branched chain fatty acid residue having 2 to 30 carbon atoms; R$_2$ represents an active ester residue selected from the group consisting of a p-nitrophenol group, a 2,4-dinitriphenol group, a 2,4,5-trichlorophenol group, a pentachlorophenol group, a pentafluorophenol group, a thiophenol group, an N-hydroxysuccinimido group, an N-hydroxybenzotriazole group, an N-hydroxy-5-norbornene-2,3-dicarboximido group, an N-hydroxyphthalimido group, an N-hydroxymorpholine group, an N-hydroxypiperidine group, a 2-mercaptopyridine group, a 2-hydroxypyridine group, a 3-hydroxypyridine group, an 8-hydroxyquinoline group and a 2-hydroxyphenol group; and "Acyl" represents an acyl group having 2 to 6 carbon atoms.

2. The muramyldipeptide derivative as claimed in claim 1, wherein $R_2$ represents an N-hydroxy-5-norbornene-2,3-dicarboximido group, a 2-hydroxypyridine group or a 3-hydroxypyridine group.

3. 6-O-Acetyl-N-acetylmuramyl-L-alanyl-D-isoglutamine 1-succinimidyl ester.

4. 6-O-Butyryl-N-acetylmuramyl-L-alanyl-D-isoglutamine 5-norbornene-2,3-dicarboxyimidyl ester.

5. 6-O-Hexanoyl-N-acetylmuramyl-L-alanyl-D-isoglutamine 5-norbornene-2,3-dicarboxyimidyl ester.

6. p-Toluenesulfonic acid salt of 6-O-Octanoyl-N-acetylmuramyl-L-alanyl-D-isoglutamine 3-pyridyl ester.

7. 6-O-(2-Tetradecylhexadecanoyl)-N-acetylmuramyl-L-alanyl-D-isoglutamine 5-norbornene-2,3-dicarboxyimidyl ester.

8. 6-O-Butyryl-N-acetylmuramyl-L-alanyl-D-isoglutamine p-nitrophenyl ester.

* * * * *